United States Patent [19]
Jung et al.

[11] Patent Number: 6,059,544
[45] Date of Patent: *May 9, 2000

[54] IDENTIFICATION SYSTEM FOR A SURGICAL CASSETTE

[75] Inventors: Christopher C. Jung, Mission Viejo; Nader Nazarifar, Laguna Hills, both of Calif.

[73] Assignee: Alcon Laboratories, Inc., Fort Worth, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/700,917

[22] Filed: Aug. 21, 1996

Related U.S. Application Data

[63] Continuation-in-part of application No. 08/566,341, Dec. 1, 1995.

[51] Int. Cl.$^7$ .............................. F04B 43/12; A61M 1/00
[52] U.S. Cl. ............................................ 417/477.2; 604/30
[58] Field of Search ............................ 417/477.2; 604/30

[56] References Cited

U.S. PATENT DOCUMENTS

| | | |
|---|---|---|
| 4,395,258 | 7/1983 | Wang et al. . |
| 4,493,695 | 1/1985 | Cook . |
| 4,627,833 | 12/1986 | Cook . |
| 4,713,051 | 12/1987 | Steppe et al. . |
| 4,758,238 | 7/1988 | Sundblom et al. . |
| 4,790,816 | 12/1988 | Sundblom et al. . |
| 4,798,580 | 1/1989 | DeMeo et al. . |
| 5,207,647 | 5/1993 | Phelps ...................................... 604/158 |
| 5,246,422 | 9/1993 | Favre . |
| 5,267,956 | 12/1993 | Beuchat . |
| 5,364,342 | 11/1994 | Beuchat et al. . |
| 5,403,277 | 4/1995 | Dodge et al. .............................. 604/30 |
| 5,429,602 | 7/1995 | Hauser ..................................... 604/65 |
| 5,436,418 | 7/1995 | Tamehira . |
| 5,460,490 | 10/1995 | Carr et al. ............................ 417/477.2 |
| 5,518,378 | 5/1996 | Neftel et al. ......................... 417/477.2 |

FOREIGN PATENT DOCUMENTS

| | | |
|---|---|---|
| 0 320 168 | 6/1989 | European Pat. Off. . |
| WO 95/28190 | 10/1995 | WIPO . |

*Primary Examiner*—Timothy Thorpe
*Assistant Examiner*—Ehud Gartenberg
*Attorney, Agent, or Firm*—Jeffrey S. Schira

[57] ABSTRACT

A cassette having, in a first embodiment, a series of break-off, prismatic tabs integrally formed in the cassette that can be optically sensed by the surgical instrument.

1 Claim, 12 Drawing Sheets

6,059,544

IDENTIFICATION SYSTEM FOR A SURGICAL CASSETTE

This application is a continuation-in-part of U.S. pat. application Ser. No. 08/566,341, filed Dec. 1, 1995.

BACKGROUND OF THE INVENTION

The present invention relates to surgical cassettes and more particularly to an identification system for surgical cassettes.

The use of cassettes with surgical instruments to help manage irrigation and aspiration flows into a surgical site are well-known. U.S. Pat. Nos. 4,493,695, 4,627,833 (Cook), 4,395,258 (Wang, et al.), 4,713,051 (Steppe, et al.), 4,798,850 (DeMeo, et al.), 4,758,238, 4,790,816 (Sundblom, et al.) and 5,267,956, 5,364,342 (Beuchat) all disclose tubeless or tube-type surgical cassettes and are incorporated herein in their entirety by reference.

The fluidic performance of the surgical instrument is substantially affected by the fluidic performance of the cassette. As a result, prior art surgical instruments and cassettes are designed to work as an integral system, with the fluidic performance of the cassette designed to optimize the fluidic performance of the entire surgical system. This integral design concept has required that prior art surgical instruments be used with only one specific cassette, and that any given cassette interacts with only one type of surgical instrument.

With the advances made in the last few years in digital circuitry, it is desirable to design and build surgical instruments that can manually or automatically change the surgical operating parameters to suit special situations or a surgeon's specific operating preferences. Parameters such as aspiration fluid flow rate, pump speed, vacuum level, irrigation fluid pressure and irrigation fluid flow rate can be preprogrammed for a specific surgeon or surgical procedure. This increased flexibility of modern surgical instruments is somewhat limited by the inflexibility of the surgical cassette. In order to optimize the surgical system, the performance of the cassette should be optimized for the specific surgical procedure or the specific set of parameters being used by the surgeon. While a cassette with adjustable fluidics performance is one alternative, the most cost effective method of optimizing cassette performance, particularly if the cassette is intended to be discarded after a single use, is to design a different cassette for each surgical procedure or set of operating parameters, however; the use of different cassettes requires that the instrument "recognize" the type of cassette being used.

Accordingly, a need exists for a cassette identification system.

BRIEF DESCRIPTION OF THE INVENTION

The present invention includes any of a variety of tube-type or tubeless surgical cassettes having, in a first embodiment, a series of break-off, prismatic tabs that can be mechanically or optically sensed by the surgical instrument. In a second embodiment, a surgical cassette contains a series of identifying bar codes that can be optically scanned by the surgical instrument.

Accordingly, one objective of the present invention is to provide a surgical cassette having a series of break-off tabs.

Another objective of the present invention is to provide a surgical cassette having a series of identifying bar codes.

Still another objective of the present invention is to provide a surgical cassette having a magnetic strip.

These and other objectives and advantages of the present invention will become apparent from the detailed description and claims which follow.

DETAILED DESCRIPTION OF THE INVENTION

Figure 1:
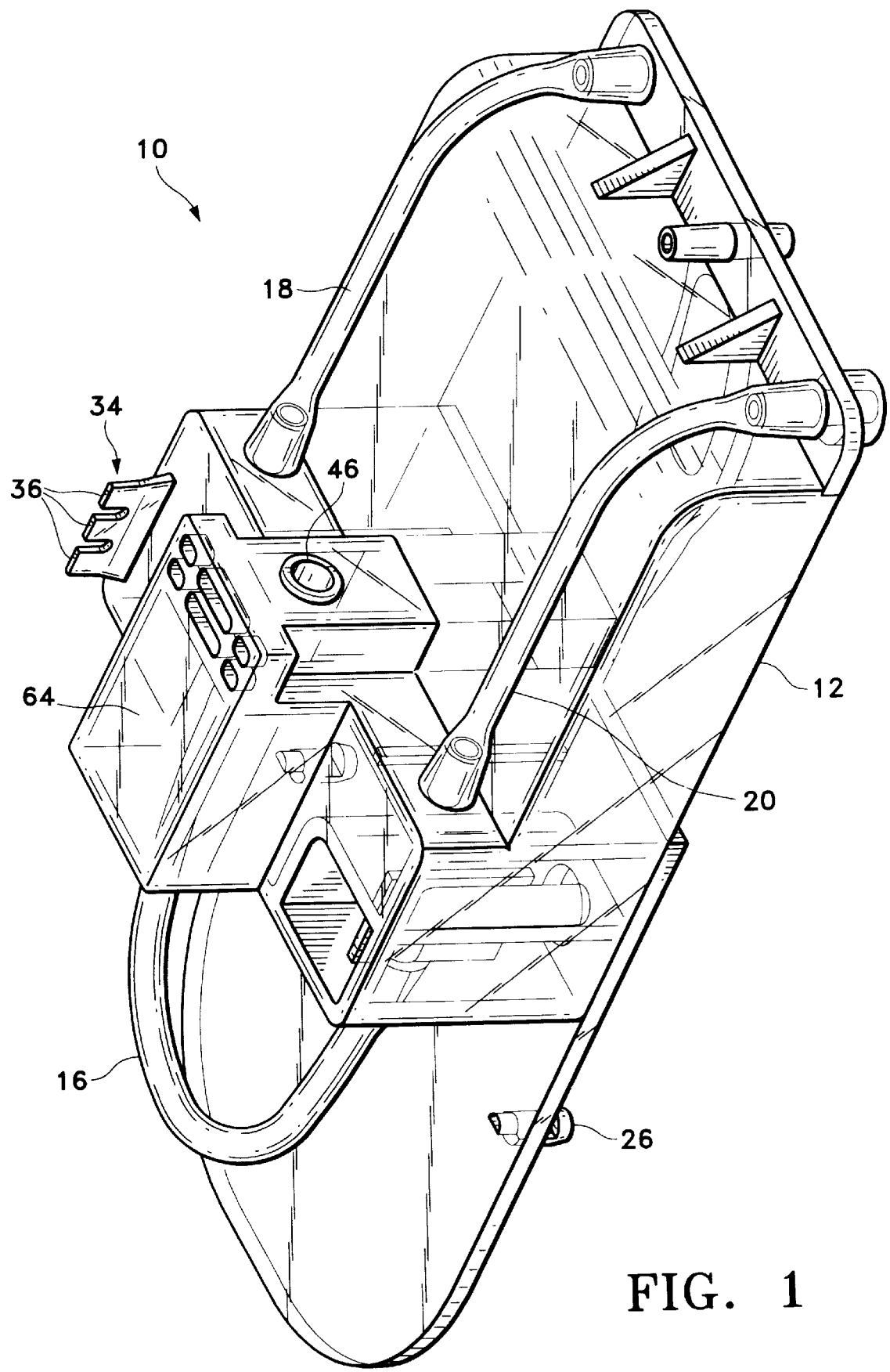
FIG. 1 is a top, left-hand perspective view of one embodiment of the present invention.
Figure 2:
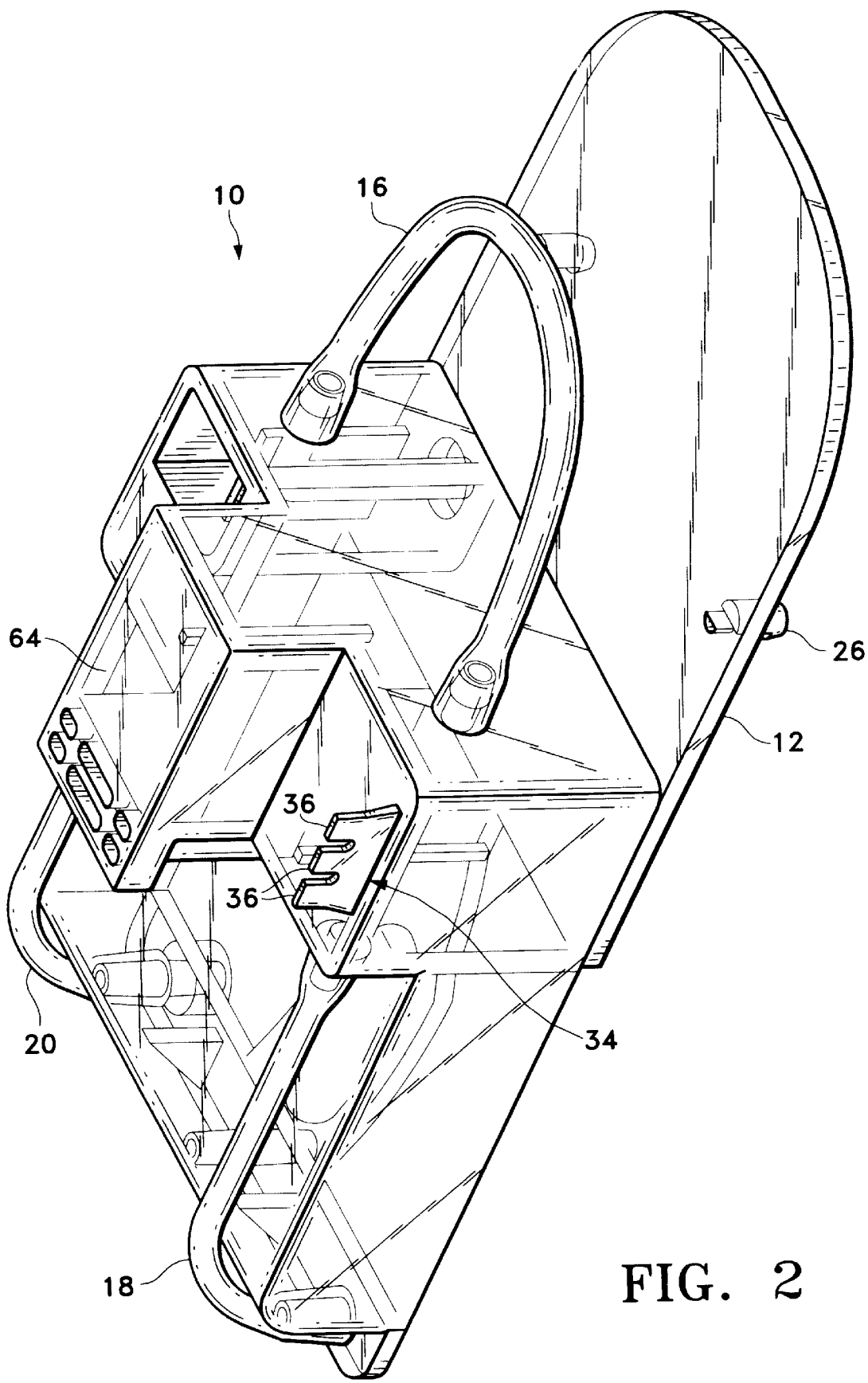
FIG. 2 is a bottom, right-hand perspective view of the cassette illustrated in FIG. 1.
Figure 3:
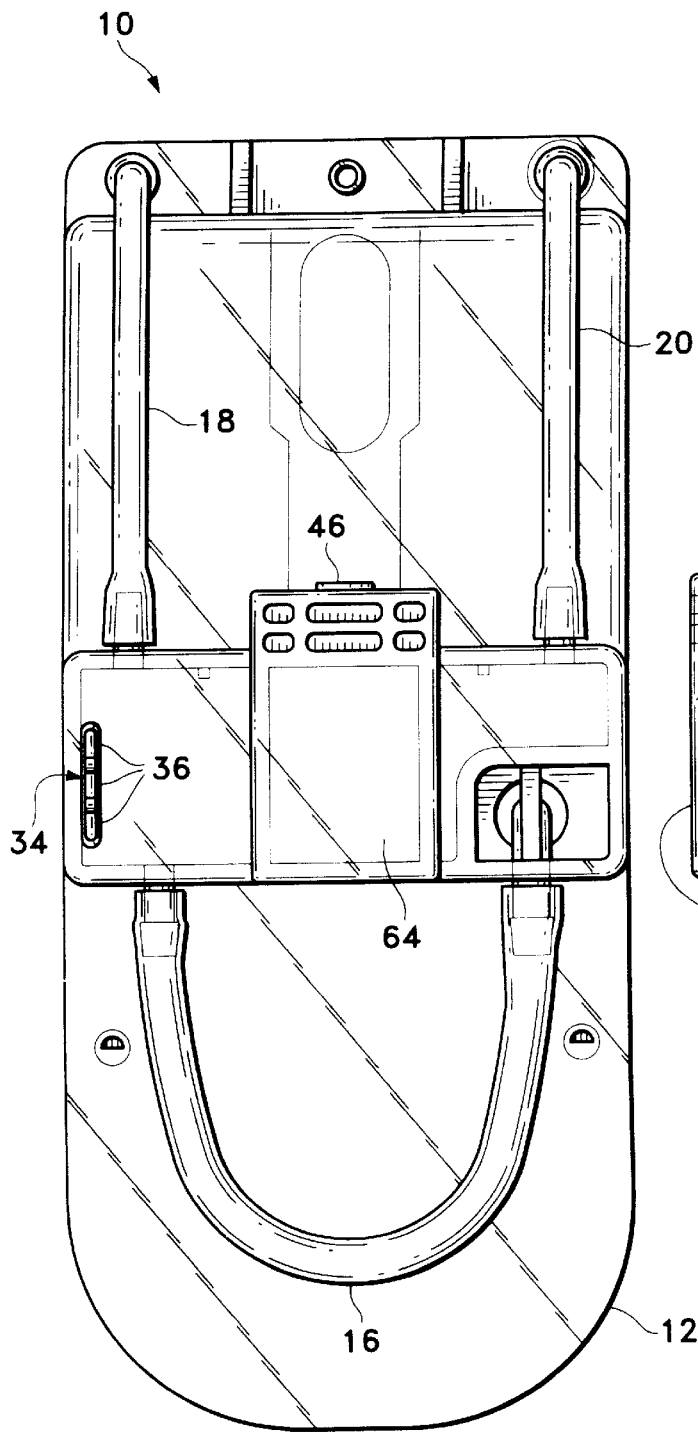
FIG. 3 is a rear, elevational view of the cassette illustrated in FIG. 1.
Figure 4:
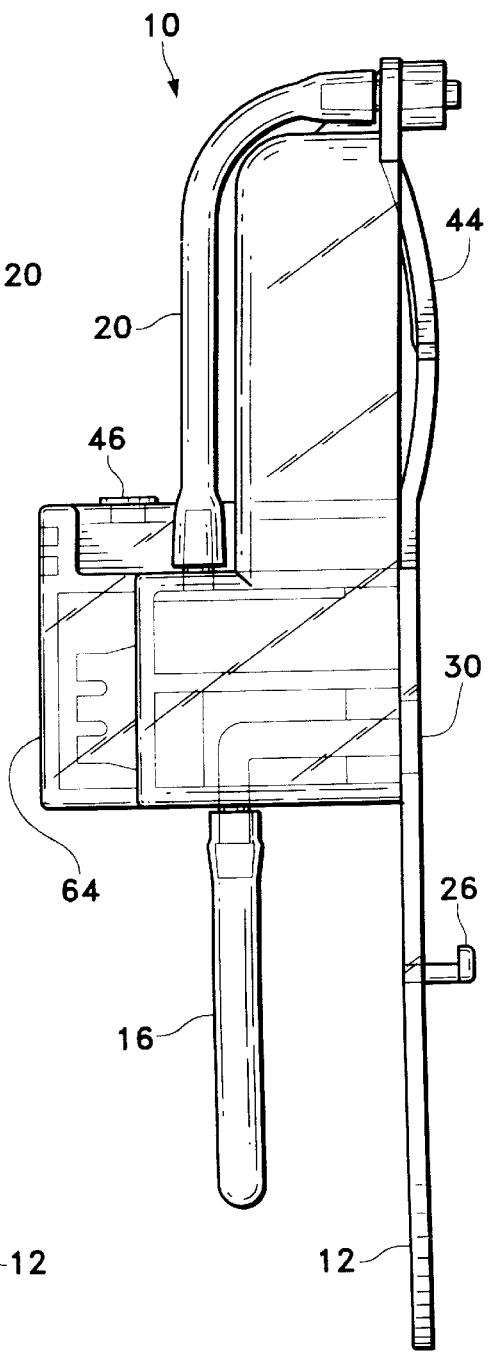
FIG. 4 is a left side, elevational view of the cassette illustrated in FIG. 1.
Figure 5:
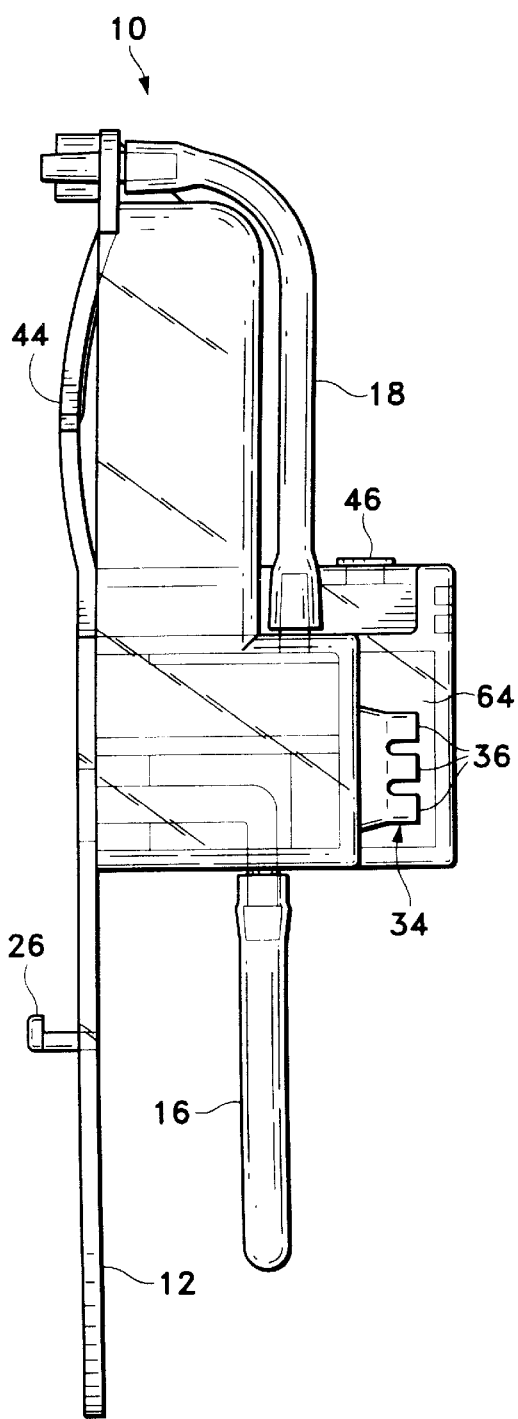
FIG. 5 is a right side, elevational view of the cassette illustrated in FIG. 1.
Figure 6:
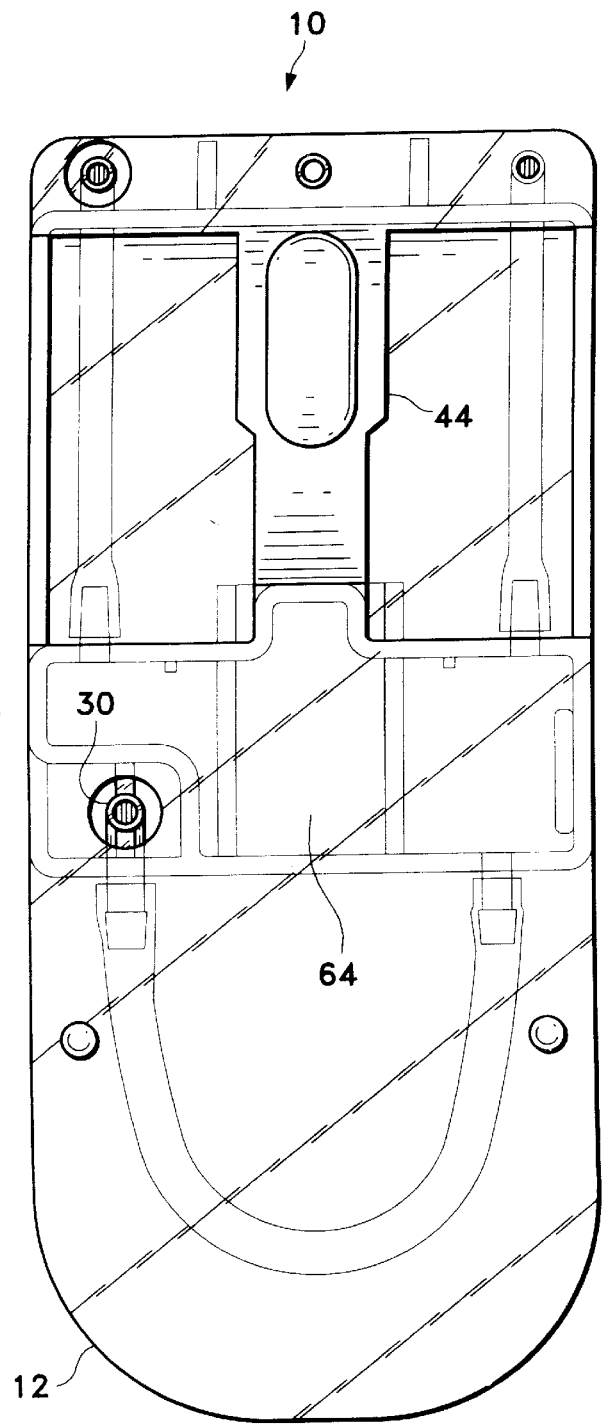
FIG. 6 is a front, elevational view of the cassette illustrated in FIG. 1.
Figure 7:
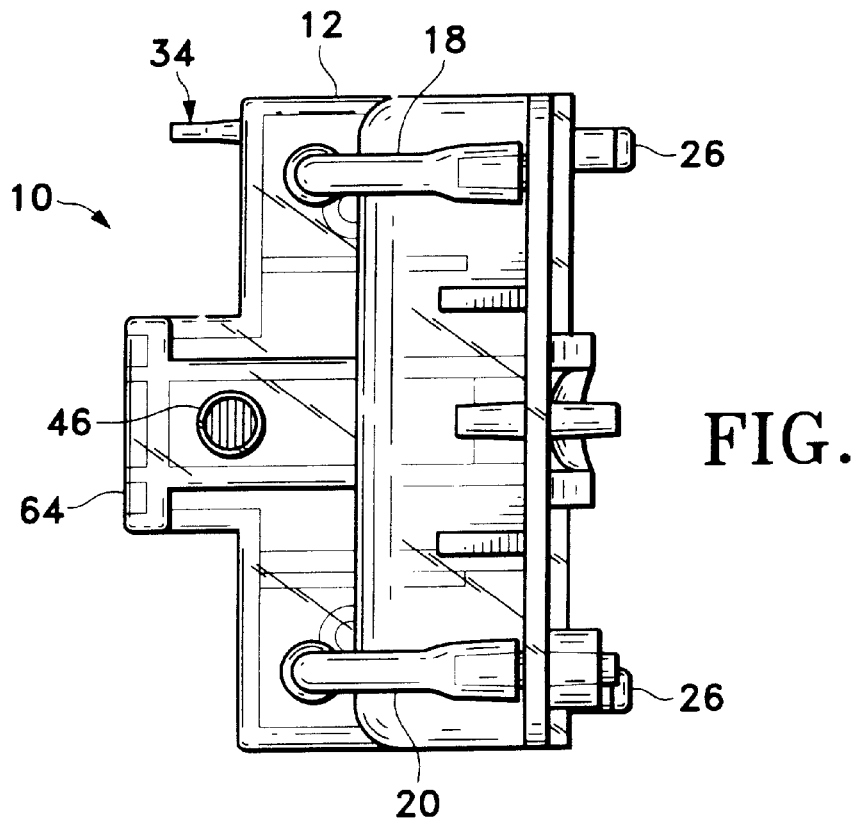
FIG. 7 is a top, plan view of the cassette illustrated in FIG. 1.
Figure 8:
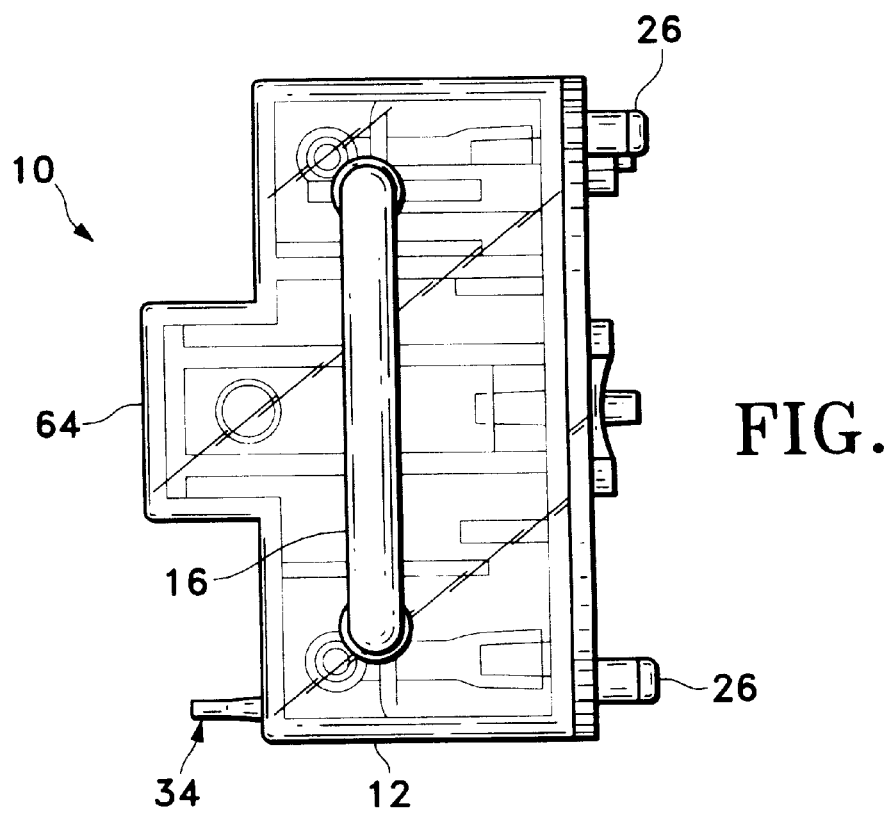
FIG. 8 is a bottom, plan view of the cassette illustrated in FIG. 1.
Figure 9:
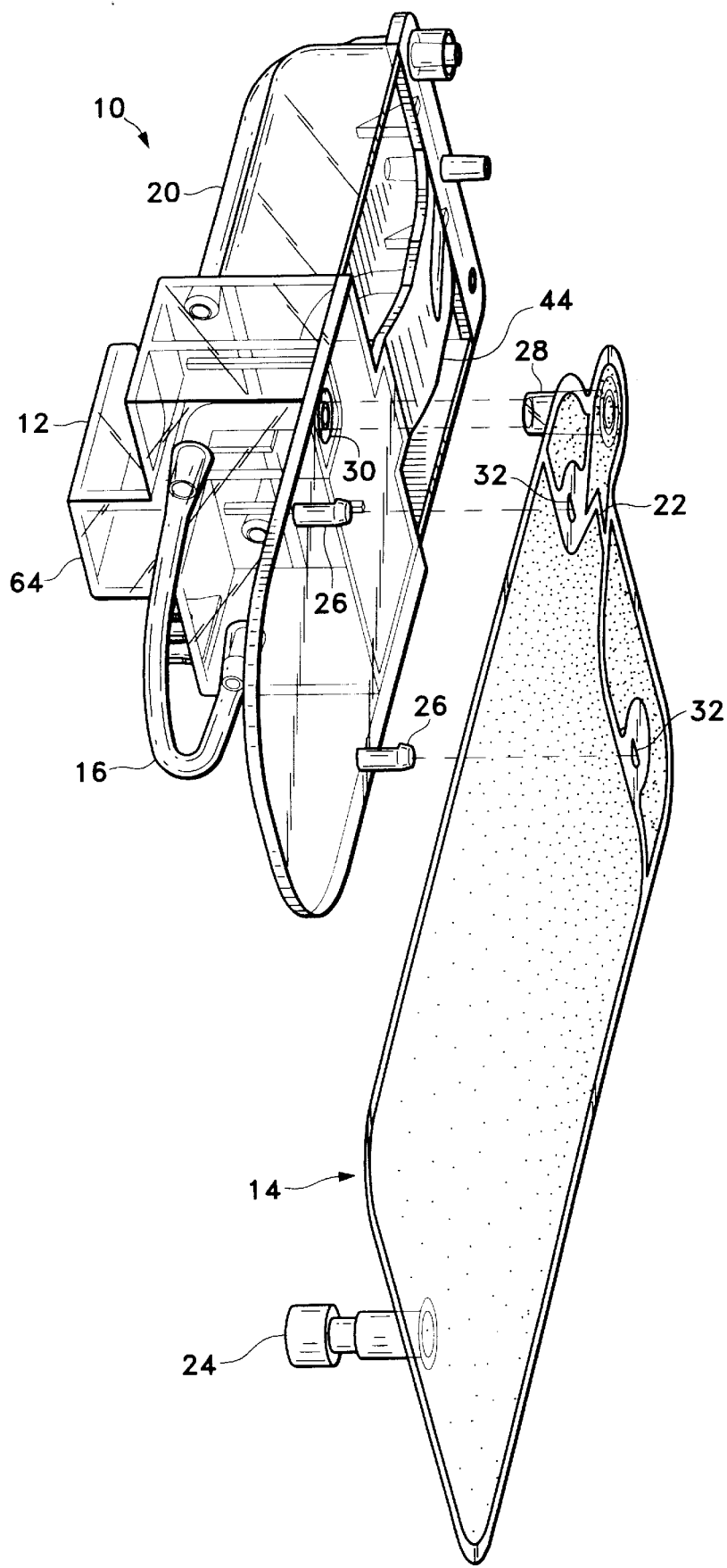
FIG. 9 is an exploded perspective view of the cassette illustrated in FIG. 1 including the drain bag.

As seen in FIGS. 1–8, cassette 10 of the present invention generally comprises housing 12, drain bag 14, peristaltic pump tube 16 and aspiration lines 18 and 20. Housing 12 may be injection molded plastic and formed in a single piece. Housing 12 may contain handle 44, for assisting in installing and removing cassette 10 in the instrument 11 and may contain vacuum inlet port 46. Drain bag 14 may be made from plastic film and preferably contains one-way valve 22 and sampling port 24. Holes 32 allow drain bag 14 to hang from hooks 26 located on housing 12, so that port 28 connects to output port 30 of peristaltic pump tube 16. Tube 16 and lines 18 and 20 may be made of any suitable material, but silicone rubber is preferred.

Figure 11:
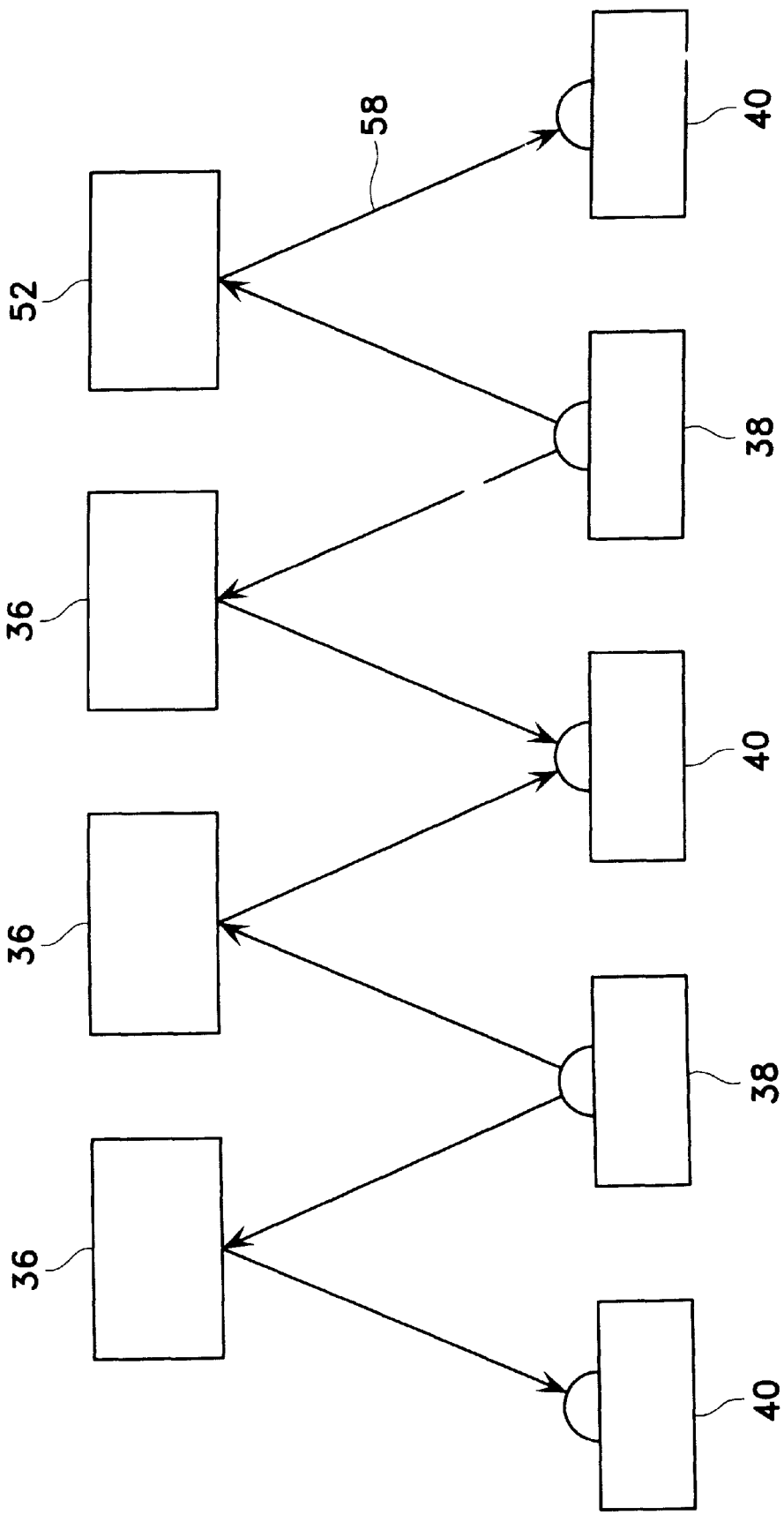
FIG. 11 is a schematic illustration of the optical reading array that may be used with the first embodiment of the present invention.

As best seen in FIGS. 1, 2, 3, 5, 7 and 8, associated with housing 12 is cassette identification system 34. In the embodiment illustrated in FIGS. 1, 2, 3, 5, 7 and 8, system 34 consists of a plurality of tabs 36 integrally molded with housing 12. While any number of tabs 36 may be used, three tabs 36 are illustrated. Tabs 36 are formed so as to be easily removed or broken off in a variety of different patterns. In use, when cassette 10 is installed in surgical instrument 11, the pattern of tabs 36 can be read easily by the instrument by various means well-known in the art. For example, the pattern of tabs 36 can be read mechanically by depressing a plurality of switches, buttons or levers (not shown) within the instrument. Such a system is disclosed in U.S. Pat. No. 5,436,418, the entire contents of which is incorporated herein by reference. In a preferred embodiment, as illustrated in FIG. 11, the pattern of tabs 36 is read optically by the use of an array of infrared light emitting diodes ("LEDs") 38 and phototransistors 40. LEDs 38 and phototransistor 40 may be any suitable I.R. photodiode/phototransistor pair such as use, LEDs 38 emit light that is reflected by tabs 36. The reflection pattern is sensed by phototransistors 40 and correlated to the presence or absence of tabs 36 and, correspondingly, the pattern of tabs 36. By using a unique pattern of tabs 36 for each type of cassette being used, the instrument is able to recognize the type of cassette installed in the instrument.

To improve the signal to noise ratio, LEDs 38 may be pulsed at a higher current level than that allowed for continuous illumination (e.g., 500 mA versus 50 mA) in order to override any stray background noise levels from sources such as sunlight, room light and other lights within the instrument.

Preferably LEDs 38 are sequentially cycled on and off by a microcontroller (not shown) to eliminate crosstalk. The width of the LED pulse is a function of the phototransistor turn-on characteristic, which tends to be larger with increasing sense resistor values. The time between adjacent pulses is a function of the turn-off characteristic, which also varies with the sense resistor value, and tends to be longer than the turn-on value.

Figure 14:
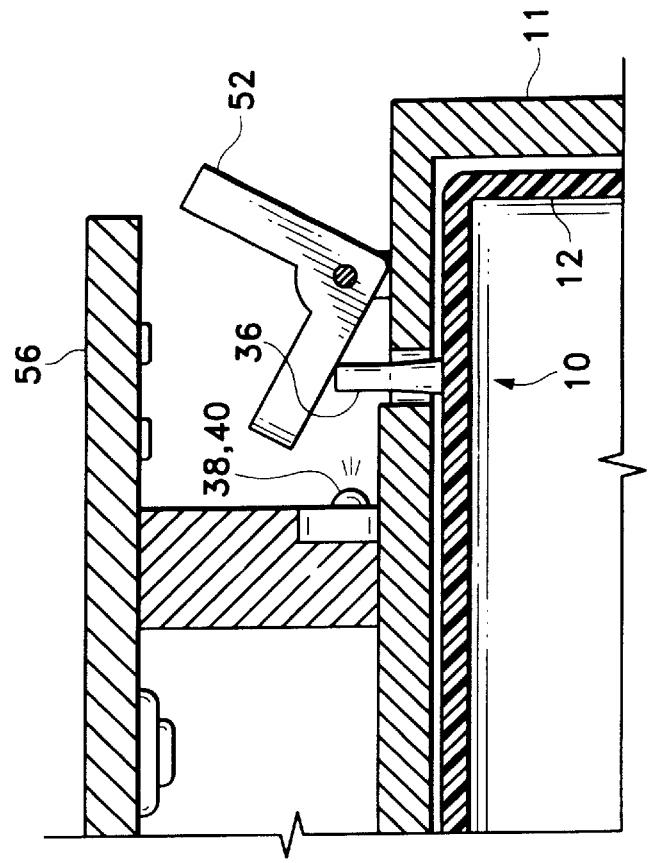
FIG. 14 is a partial cross-sectional view of the cassette receiving portion of a surgical instrument suitable for use with the first embodiment of the invention similar to FIG. 13 showing the cassette installed.
Figure 13:
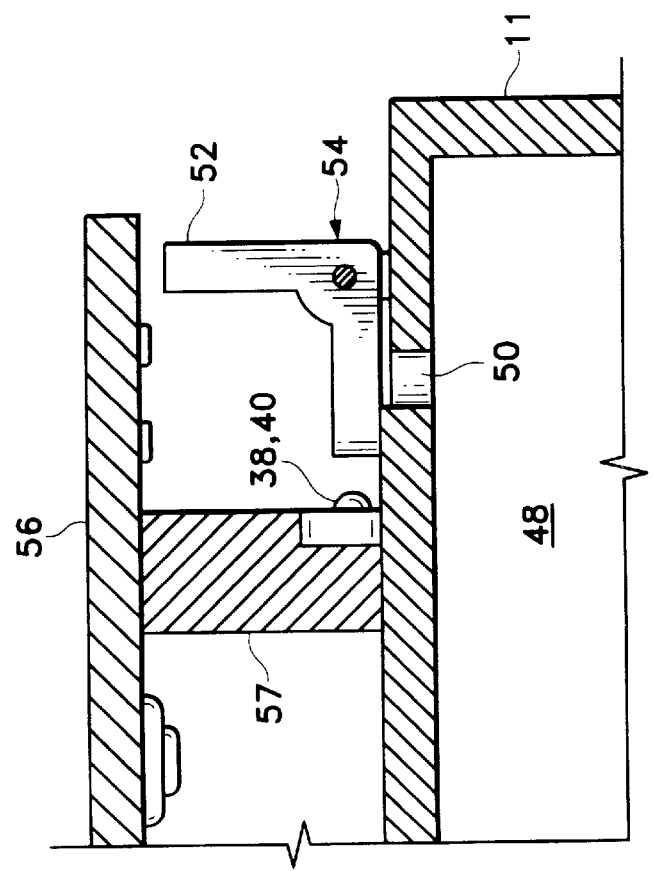
FIG. 13 is a partial cross-sectional view of the cassette receiving portion of a surgical instrument suitable for use with the first embodiment of the invention.

As can be seen in FIGS. 13 and 14, in the first embodiment of the present invention, surgical instrument 11 contains cassette receiving portion 48 with tab receiving slot 50. Slot 50 is sealed shut by door 52 that pivots about hinge 54. LEDs 38 and phototransistors 40 are mounted on circuit board 56 so as to be located near door 52 by component spacer 57. As seen in FIGS. 11 and 13, when door 52 is closed (indicating that no cassette is installed), signal 58 will be reflected back to phototransistor 40, allowing all LED/phototransistors paths to be tested. As seen in FIG. 14, when cassette 10 is installed in instrument 11, tabs 36 cause door 52 to pivot (approximately 30°) so as to scatter or absorb any light passing through tabs 36.

Figure 12:
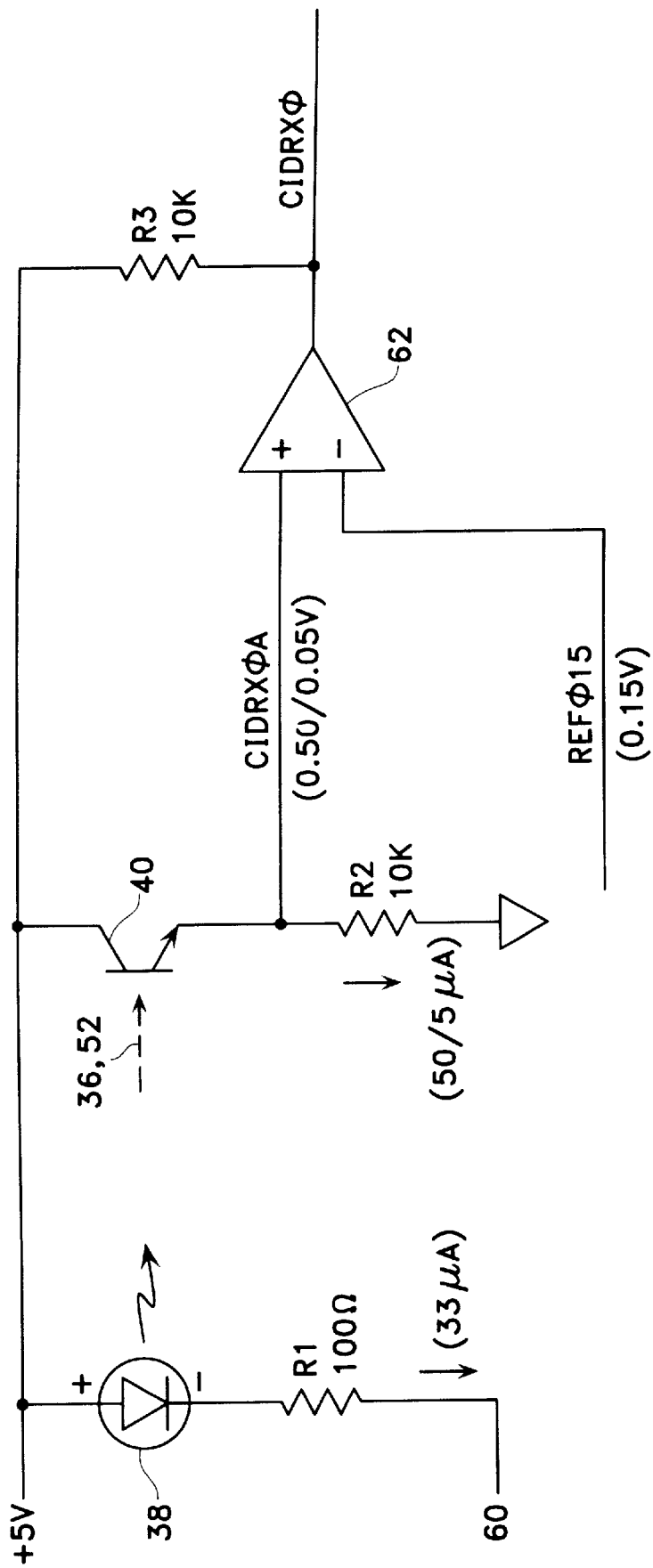
FIG. 12 is an electrical schematic illustrating one control system suitable for use with the first or third embodiment of the invention.

As can be seen in FIG. 12, LEDs 38 are illuminated by control signal 60. Light from LED 38 is reflected to phototransistor 40 by door 52 or tab 36. The output of phototransistor 40 varies with the amount of light striking phototransistor 40. At low levels, such as the reflection off of open door 52 (see FIG. 14), the current generated by phototransistor 40 has been found to be around 5 µA. At higher levels, such as the reflection off of tabs 36 or closed door 52 (see FIG. 13), the current generated by phototransistor 40 has been found to be approximately 50 µA. Sense resistor R2 transforms the signal generated by phototransistor 40 into 0.05V and 0.50V, respectively. Voltage comparator 62 compares the transformed signal with a 0.15V reference signal. This process is repeated sequentially for each LED 38.

As seen in FIGS. 1–9, in use, vacuum is introduced into fluid chamber 64 in cassette 10 through vacuum port 46. Chamber 64 communicates with lines 18 and 20, allowing material to be draw into chamber 64 through lines 18 and 20. When the material in chamber 64 reaches a certain level, a sensor (not shown) causes a peristaltic pump roller head (not shown) contained in surgical instrument 11 to rotate within pump tube 16, thereby pumping material out of chamber 64 and into bag 14.

Figure 10:
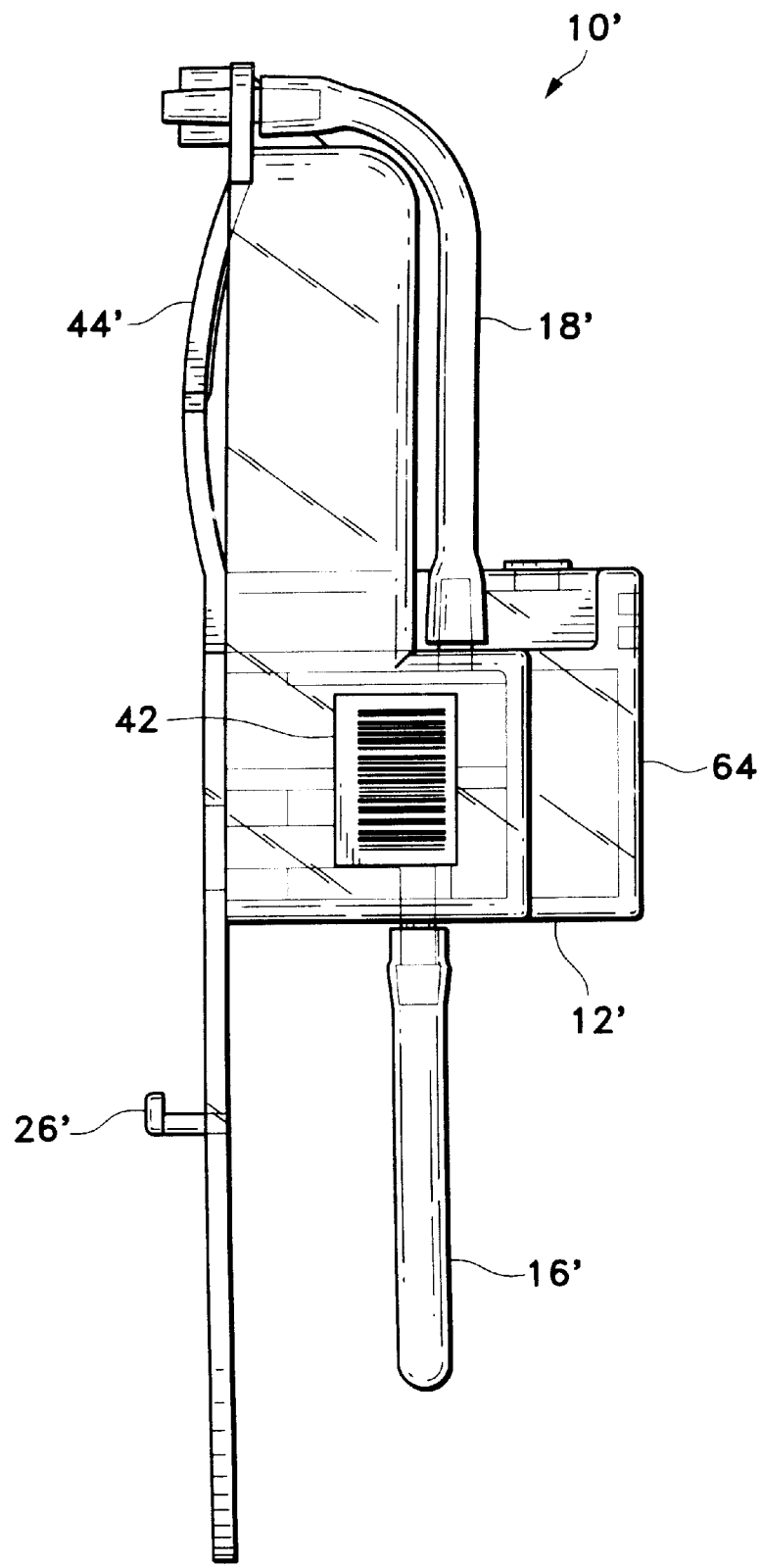
FIG. 10 is a right side, elevational view similar to FIG. 5 of a second embodiment of the present invention.

In a second embodiment illustrated in FIG. 10, tabs 36 are not used. Instead, system 34 consists of a bar code pattern 42 affixed to housing 12 that may be optically read by an optical scanner within the instrument, such optical scanners being well-known in the art.

Figure 15:
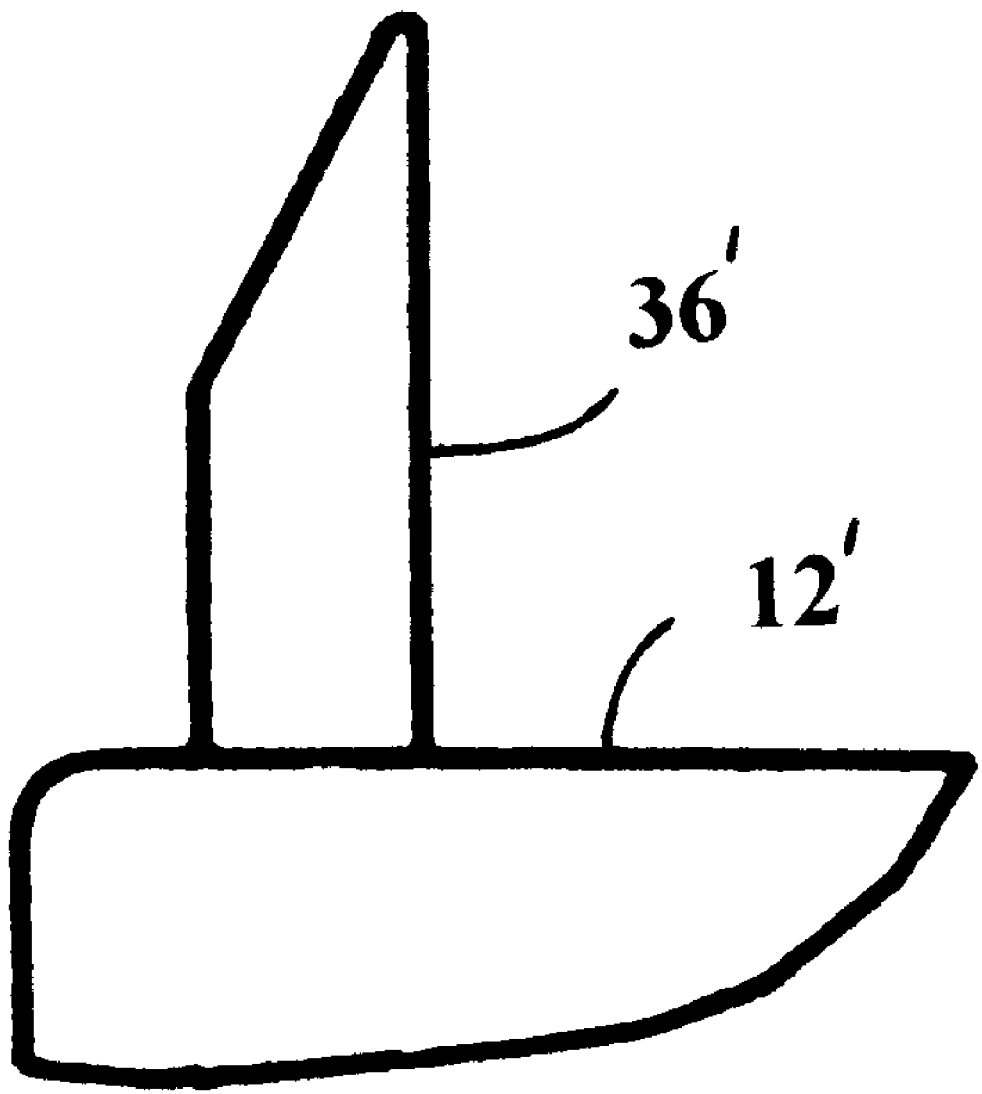
FIG. 15 is an elevational view of a prismatic tab that may be used with the present invention.
Figure 16:
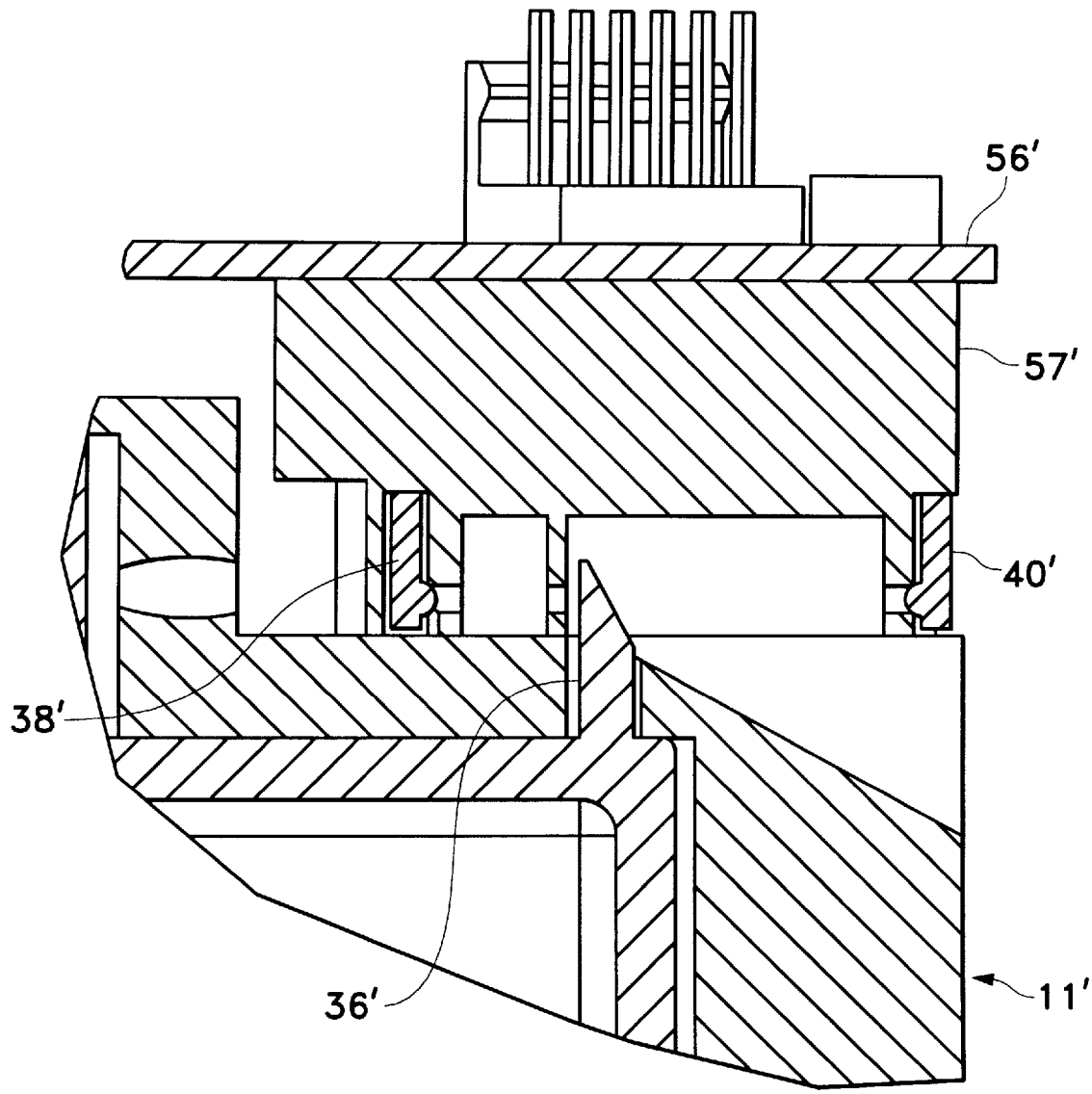
FIG. 16 is a partial cross-sectional view of the cassette receiving portion of a surgical instrument suitable for use with the third embodiment of the invention, and similar to FIG. 13, showing the cassette installed.

In a third embodiment of the present invention, illustrated in FIGS. 15 and 16, tabs 36' preferably are tapered or prismatic in shape. Preferably, the portion of tabs 36' nearest to housing 12' is of uniform thickness (e.g. 0.090 inches), with the remainder of tabs 36' gradually decreasing in thickness to around 0.010 inches. Tabs 36' preferably are approximately 0.30 inches long, with approximately one half being of uniform thickness. In this embodiment, LEDs 38' and phototransistors 40' are mounted on circuit board 56' so as to be located on opposite sides of tabs 36'. When tabs 36' are present, the prismatic shape of tabs 36' scatters or deflects the light being emitted by LEDs 38' so that little of the light is detected by phototransistors 40'. When tabs 36' are not present, much of the light being emitted by LEDs 38' is detected by phototransistors 40'. In this way, LEDs 38' and phototransistors 40' can detect the presence of tabs 36'.

This description is given for purposes of illustration and explanation. It will be apparent to those skilled in the relevant art that changes and modifications may be made to the invention described above without departing from its scope or spirit.

We claim:

1. A surgical cassette identification system for a surgical system having a set of surgical cassettes, each member of the set having a distinct row of prismatic tabs, a peristaltic pump, an array of light emitting diodes being pulsed on and off sequentially by electric circuitry to emit light and a corresponding array of phototransistors for sensing light being reflected by the tabs when the tabs are illuminated by the light emitting diode array, a computer being capable of controlling external electronic circuitry in the form of electronic output commands and accepting input from external electronic circuitry, the light emitting diodes array being connected to and controlled by the computer, the phototransistor array being connected and inputing its output to the computer, the computer being capable of identifying patterns of input signals from the phototransistor array, the input signal patterns being indicative of the light emitting diode light being reflected from the individual tabs in the prismatic tab rows, the computer further being capable of an indication that is associated with one of the input signal patterns, the improvement consisting of:

a) each of the tabs being easily and selectably breakable manually to form patterns of tabs and voids; and b) each of the patterns of tabs and voids being indicative of one distinct cassette within the set of surgical cassettes.

* * * * *